US00PP29187P3

(12) United States Plant Patent
Jacobs

(10) Patent No.: US PP29,187 P3
(45) Date of Patent: Apr. 3, 2018

(54) ASTER PLANT NAMED 'ZANASBLUBA'

(50) Latin Name: *Symphyotrichum novi-belgii*
Varietal Denomination: Zanasbluba

(71) Applicant: Henricus Cornelius Maria Jacobs, Bleiswijk (NL)

(72) Inventor: Henricus Cornelius Maria Jacobs, Bleiswijk (NL)

(73) Assignee: Chrysanthemum Breeders Association Research B.V., Rijsenhout (NL)

( * ) Notice: Subject to any disclaimer, the term of this patent is extended or adjusted under 35 U.S.C. 154(b) by 51 days.

(21) Appl. No.: 15/330,011

(22) Filed: Jul. 25, 2016

(65) Prior Publication Data

US 2018/0027718 P1 Jan. 25, 2018

(51) Int. Cl.
*A01H 5/02* (2006.01)

(52) U.S. Cl.
USPC ..... Plt./355
CPC ..... *A01H 5/025* (2013.01)

(58) Field of Classification Search
USPC ..... Plt./355
See application file for complete search history.

*Primary Examiner* — Keith O Robinson
(74) *Attorney, Agent, or Firm* — C. A. Whealy

(57) ABSTRACT

A new and distinct cultivar of Aster plant named 'Zanasbluba', characterized by its compact, upright to slightly spreading and mounding plant habit; moderately vigorous growth habit; freely branching growth habit; dense and bushy appearance; freely flowering habit; double-type inflorescences with violet to violet blue-colored ray florets; good postproduction longevity and good container performance.

2 Drawing Sheets

Botanical designation: *Symphyotrichum novi-belgii*.
Cultivar denomination: 'ZANASBLUBA'.

BACKGROUND OF THE INVENTION

The present invention relates to a new and distinct cultivar of Aster plant, botanically known as *Symphyotrichum novi-belgii* and hereinafter referred to by the name 'Zanasbluba'.

The new Aster plant is a product of a planned breeding program conducted by the Inventor in Rijsenhout, The Netherlands. The objective of the breeding program is to create new compact Aster plants with freely branching habit and attractive double-type inflorescences.

The new Aster originated from an open-pollination in September, 2012 in Rijsenhout, The Netherlands of a proprietary selection of *Symphyotrichum novi-belgii* identified as code number 676, not patented, as the female, or seed, parent with an unknown selection of *Symphyotrichum novi-belgii*, as the male, or pollen, parent. The new Aster plant was discovered and selected by the Inventor as a single flowering plant within the progeny of the stated open-pollination in a controlled greenhouse environment in Rijsenhout, The Netherlands in April, 2013.

Asexual reproduction of the new Aster plant by terminal vegetative cuttings was first conducted in Rijsenhout, The Netherlands in May, 2013. Asexual reproduction by cuttings has shown that the unique features of this new Aster plant are stable and reproduced true to type in successive generations.

SUMMARY OF THE INVENTION

Plants of the new Aster have not been observed under all possible combinations of environmental conditions and cultural practices. The phenotype may vary somewhat with variations in environmental conditions such as temperature, daylength and light intensity, without, however, any variance in genotype.

The following traits have been repeatedly observed and are determined to be the unique characteristics of 'Zanasbluba'. These characteristics in combination distinguish 'Zanasbluba' as a new and distinct Aster plant:

1. Compact, upright to slightly spreading and mounding plant habit.
2. Moderately vigorous growth habit.
3. Freely branching growth habit; dense and bushy appearance.
4. Freely flowering habit.
5. Double-type inflorescences with violet to violet blue-colored ray florets.
6. Good postproduction longevity and good container performance.

Plants of the new Aster differ primarily from plants of the female parent selection in inflorescence form as plants of the female parent selection have semi-double type inflorescences.

Plants of the new Aster can be compared to plants of *Symphyotrichum novi-belgii* 'Dasgra', disclosed in U.S. Plant Pat. No. 23,828. In side-by-side comparisons, plants of the new Aster differ from plants of 'Dasgra' in the following characteristics:

1. Plants of the new Aster flower earlier than plants of 'Dasgra'.
2. Plants of the new Aster are more freely flowering than plants of 'Dasgra'.

BRIEF DESCRIPTION OF THE PHOTOGRAPHS

The accompanying photographs illustrate the overall appearance of the new Aster plant showing the colors as true as it is reasonably possible to obtain in colored reproductions of this type. Colors in the photographs may differ slightly from the color values cited in the detailed botanical description which accurately describe the colors of the new Aster plant.

The photograph on the first sheet is a side perspective view of a typical flowering plant of 'Zanasbluba' grown in a container.

The photograph on the second sheet is a close-up view of a typical flowering plant of 'Zanasbluba'.

DETAILED BOTANICAL DESCRIPTION

The aforementioned photographs and following observations and measurements describe plants grown during the late winter and early spring in 12-cm containers in a glass-covered greenhouse in Rijsenhout, The Netherlands and under cultural practices typical of commercial Aster production. During the production of the plants, day temperatures ranged from 18.5° C. to 22° C., night temperatures ranged from 18° C. to 21° C. and light levels ranged from 3,500 to 7,000 lux. Plants were pinched one time and were ten weeks old when the photographs and description were taken. In the following description, color references are made to The Royal Horticultural Society Colour Chart, 2001 Edition, except where general terms of ordinary dictionary significance are used.

Botanical classification: *Symphyotrichum novi-belgii* 'Zanasbluba'.

Parentage:

*Female, or seed, parent*.—Proprietary selection of *Symphyotrichum novi-belgii* identified as code number 676, not patented.

*Male, or pollen, parent*.—Unknown selection of *Symphyotrichum novi-belgii*, not patented.

Propagation:

*Type*.—Terminal vegetative cuttings.

*Time to initiate roots, summer*.—About seven days at temperatures about 21° C.

*Time to produce a rooted young plant, summer*.—About nine to ten days at temperatures about 21° C.

*Time to produce a rooted young plant, autumn*.—About eleven to twelve days at temperatures about 21° C.

*Root description*.—Fine, fibrous; close to 155D and 199D in color.

*Rooting habit*.—Freely branching; dense.

Plant description:

*Plant and growth habit*.—Herbaceous double-type potted Aster plant; compact, upright to slightly spreading and mounding plant habit; moderately vigorous growth habit; freely branching growth habit; dense and bushy appearance; pinching enhances branching potential.

*Plant height*.—About 14 cm to 15 cm.

*Plant width*.—About 16 cm to 18 cm.

*Lateral branches*.—Length: About 11 cm to 12 cm. Diameter: About 8 mm to 10 mm. Internode length: About 4 mm to 5 mm. Aspect: About 50° from vertical. Strength: Strong. Texture and luster: Pubescent; matte. Color: Close to 139B.

Leaf description:

*Arrangement*.—Alternate, simple; sessile.

*Length*.—About 4 cm to 5 cm.

*Width*.—About 9 mm to 11 mm.

*Shape*.—Elliptic.

*Apex*.—Acute.

*Base*.—Attenuate.

*Margin*.—Entire.

*Texture and luster, upper and lower surfaces*.—Somewhat rough, pubescent; semi-glossy.

*Color*.—Developing leaves, upper surface: Close to 137A. Developing leaves, lower surface: Close to 137C. Fully expanded leaves, upper surface: Close to 136A; venation, close to 137C. Fully expanded leaves, lower surface: Close to 147D; venation, 148D.

Inflorescence description:

*Type and arrangement*.—Double-type (or decorative) inflorescence form with lanceolate-shaped ray florets; inflorescences borne on terminal and axillary branches above and beyond the foliar plane; ray and disc florets arranged acropetally on a capitulum; inflorescences face mostly upright to slightly outwardly.

*Fragrance*.—None detected.

*Flowering response*.—Under natural conditions, plants flower during the autumn in The Netherlands; plants begin flowering about six weeks after planting.

*Inflorescence longevity*.—Inflorescences maintain good substance for about four weeks on the plant; inflorescences persistent.

*Quantity of inflorescences*.—Freely flowering habit with about eight to ten inflorescences per lateral branch and about 18 to 20 inflorescence buds and inflorescences per plant at one time.

*Inflorescence buds*.—Height: About 5 mm. Diameter: About 1 cm. Shape: Globular. Texture and luster: Smooth, glabrous; matte. Color: Close to 138A with spots, close to 79C.

*Inflorescence size*.—Diameter: About 3.5 cm. Depth (height): About 1.8 cm. Diameter of disc: If present, about 1.5 cm.

*Receptacles*.—Height: About 5 mm. Diameter: About 4 mm. Shape: Conical to domed. Color: Close to 145D.

*Ray florets*.—Quantity and arrangement: About 140 to 150 arranged in numerous whorls. Length: About 1.3 cm to 1.5 cm. Width: About 1.8 mm to 2 mm. Shape: Lanceolate. Apex: Bluntly acute or emarginate. Base: Attenuate. Margin: Entire. Texture and luster, upper surface: Smooth, glabrous; semi-glossy. Texture and luster, lower surface: Smooth, glabrous; matte. Orientation: Initially upright to semi-upright to eventually close to perpendicular to the peduncle. Color: When opening, upper surface: Close to N88A. When opening, lower surface: Close to N88D. Fully opened, upper surface: Close to N88C; color becoming closer to 93B with development. Fully opened, lower surface: Close to 91D; color becoming closer to 93D with development.

*Disc florets*.—Quantity and arrangement: If present, variable in quantity and arranged at the center of the receptacle; disc florets mostly inconspicuous. Length: About 6 mm to 7 mm. Diameter: About 1 mm to 1.5 mm. Shape: Tubular, elongated; five free apices are acute. Texture and luster, inner and outer surfaces: Smooth, glabrous; slightly glossy. Color, immature, inner and outer surfaces: Close to 143C. Color, mature, inner surface: Close to 158C; color becoming closer to N77D with development. Color, mature, outer surface: Close to 145C; color becoming closer to 186D with development.

*Phyllaries*.—Quantity and arrangement: About 50 per inflorescence arranged in about five whorls. Length: About 4 mm to 5 mm. Width: About 1.5 mm. Shape: Narrowly elliptic. Apex: Acute. Base: Attenuate. Margin: Entire. Texture and luster, upper and lower surfaces: Pubescent; semi-glossy. Color, upper surface: Close to 137A. Color, lower surface: Close to 137B.

*Peduncles*.—Length: About 1.5 cm to 2 cm. Diameter: About 1 mm. Strength: Strong. Texture and luster: Pubescent; semi-glossy. Color: Close to 139A to 139B.

*Reproductive organs*.—Androecium: Present on disc florets only. Quantity of stamens per floret: Five. Filament length: About 2.5 mm. Filament color: Close to 150D. Anther shape: Lanceolate. Anther length: About 1 mm. Anther color: Close to 4A. Pollen amount: Scarce. Pollen color: Close to 17B. Gynoecium: Quantity of pistils per floret: One. Pistil length: About 8 mm. Stigma diameter: About 1.5 mm. Stigma shape: Bifurcate. Stigma color: Close to 154A, color becoming closer to 76C with development. Style length: About 3 mm to 3.5 mm. Style color: Close to 150D. Ovary color: Close to 149D.

*Seeds and fruits*.—Seed and fruit production have not been observed on plants of the new Aster.

Disease & pest resistance: Plants of the new Aster have not been observed to be resistant to pathogens and pests common to Aster plants.

Temperature tolerance: Plants of the new Aster have been observed to tolerate temperatures ranging from about 5° C. to about 32° C. to 33° C.

It is claimed:

1. A new and distinct Aster plant named 'Zanasbluba' as illustrated and described.

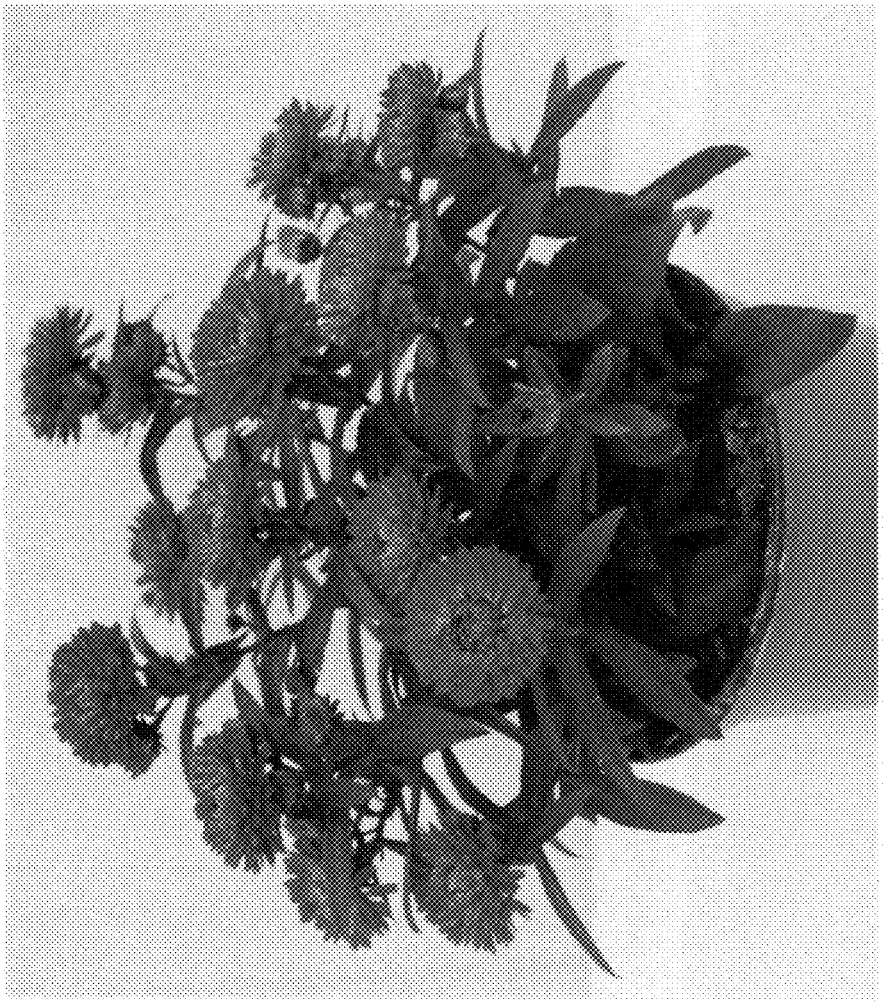

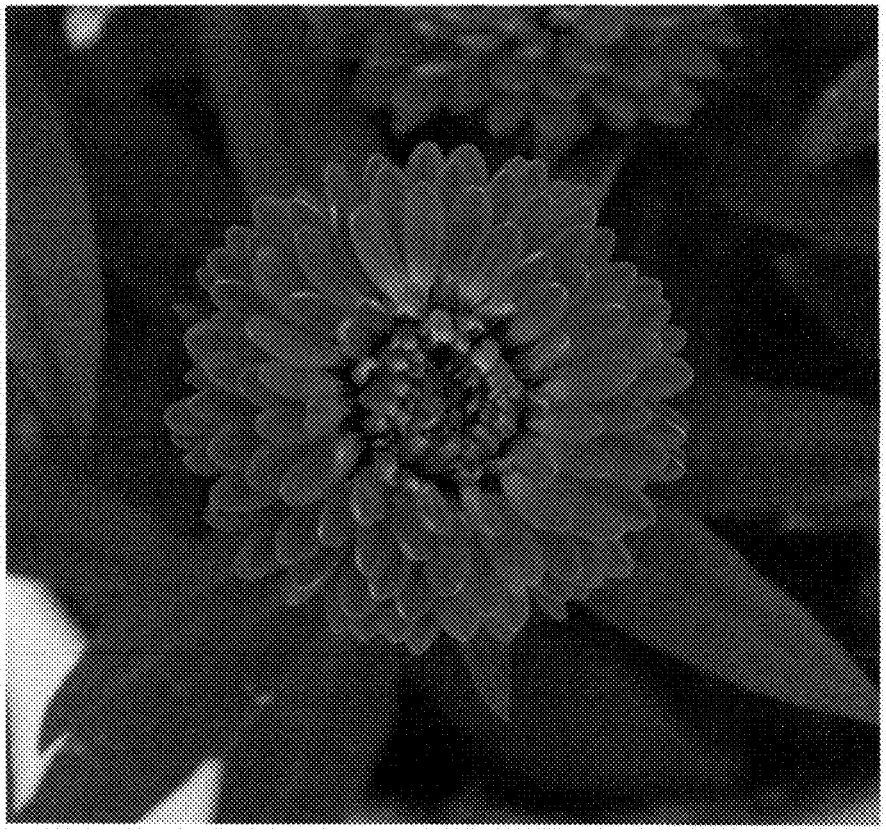

* * * * *